United States Patent [19]

Ushikubo et al.

[11] Patent Number: 5,534,650
[45] Date of Patent: Jul. 9, 1996

[54] METHOD FOR PRODUCING A NITRILE

[75] Inventors: Takashi Ushikubo; Kazunori Oshima, both of Yokohama; Tatsuya Ihara; Hiroyuki Amatsu, both of Kurashiki, all of Japan

[73] Assignee: Mitsubishi Chemical Corporation, Tokyo, Japan

[21] Appl. No.: 372,022

[22] Filed: Jan. 12, 1995

[30] Foreign Application Priority Data

Jan. 12, 1994 [JP] Japan .................................. 6-001665

[51] Int. Cl.$^6$ ............................................... C07C 253/00
[52] U.S. Cl. ........................................................ 558/319
[58] Field of Search ............................................. 558/319

[56] References Cited

U.S. PATENT DOCUMENTS

| 4,370,279 | 1/1983 | Sasaki et al. . | |
|---|---|---|---|
| 4,797,381 | 1/1989 | Bartek et al. . | |
| 4,966,990 | 10/1990 | Otake et al. . | |
| 5,049,692 | 9/1991 | Hatano et al. . | |
| 5,206,201 | 4/1993 | Kishimoto et al. . | |
| 5,231,214 | 7/1993 | Ushikubo et al. . | |
| 5,281,745 | 1/1994 | Ushikubo et al. . | |
| 5,288,473 | 2/1994 | Shaw et al. | 558/319 X |
| 5,332,855 | 7/1994 | Blanchard et al. | 558/319 |
| 5,334,743 | 8/1994 | Blanchard et al. | 558/319 |
| 5,336,804 | 8/1994 | Blanchard et al. | 558/319 |
| 5,422,328 | 6/1995 | Ushikubo et al. | 558/319 X |

FOREIGN PATENT DOCUMENTS

| 0318295 | 5/1989 | European Pat. Off. . |
|---|---|---|
| 0529853A2 | 3/1993 | European Pat. Off. . |
| 1304665 | 1/1973 | United Kingdom . |

*Primary Examiner*—Johann Richter
*Attorney, Agent, or Firm*—Oblon, Spivak, McClelland, Maier & Neustadt

[57] ABSTRACT

A method for producing a nitrile by a gas phase catalytic oxidation reaction of an alkane with ammonia in the presence of a catalyst, which comprises supplying the alkane and ammonia to an upper stream inlet of the catalyst layer, and separately supplying at least a part of the total amount of ammonia to a downstream position of the catalyst layer located downstream from the upper stream inlet of the catalyst layer.

9 Claims, 1 Drawing Sheet

5,534,650

METHOD FOR PRODUCING A NITRILE

BACKGROUND OF THE INVENTION

1. Field of the Invention

The present invention relates to a method for producing a nitrile. Particularly, it relates to an improved method for producing a nitrile using an alkane as starting material. Nitriles such as acrylonitrile and methacrylonitrile have been industrially produced as important intermediates for the preparation of fibers, synthetic resins, synthetic rubbers and the like.

2. Discussion of Background

As the most popular method for producing such nitriles, a so-called ammoxidation method has been known in which an alkene, such as propylene or isobutene, is catalytically reacted at a high temperature in a gas phase in the presence of the catalyst. On the other hand, recently, an attention has been drawn to a method wherein an inexpensive lower alkane such as propane or isobutane is used as starting materials, and it is catalytically reacted with ammonia and oxygen in a gas phase.

However, the conventional method for producing a nitrile from an alkane starting material is not fully satisfactory as the yield is still low as compared with the alkene starting material. In order to improve the yield of the nitrile, a method of adding a small amount of an organic halide, an inorganic halide or a sulfur compound to the reaction system has been attempted. However, such a method has a problem of corrosion of the reaction apparatus, and each method has a practical problem for industrial application.

According to conventional methods employing a catalyst system, not only the catalytic performance is inadequate but also it is obliged to adopt disadvantageous reaction conditions with respect to the reaction temperature or the reaction gas composition, in many cases. For example, a method for separating and recovering unreacted alkane from the desired nitrile and recycling it to the reactor, is extremely cumbersome and disadvantageous from the viewpoint of the production cost. Further, by conventional techniques, utilization efficiency of ammonia in the reaction is low, and the reaction is conducted by supplying an excess amount of ammonia, in many cases.

SUMMARY OF THE INVENTION

The present inventors have conducted various studies on a method for producing a nitrile using an alkane as starting material and as a result, have found it possible to produce a desired nitrile in a yield higher than conventional methods, by supplying ammonia separately in the reaction system in a method for producing a nitrile by a gas phase catalytic oxidation reaction of an alkane with ammonia in the presence of a catalyst. The present invention has been accomplished on the basis of this discovery.

Thus, the present invention provides a method for producing a nitrile by a gas phase catalytic oxidation reaction of an alkane with ammonia in the presence of a catalyst, which comprises supplying the alkane and ammonia to an upper stream inlet of the catalyst layer, and separately supplying at least a part of the total amount of ammonia to a downstream position of the catalyst layer located downstream from the upper stream inlet of the catalyst layer.

DETAILED DESCRIPTION OF THE PREFERRED EMBODIMENTS

Figure 1:
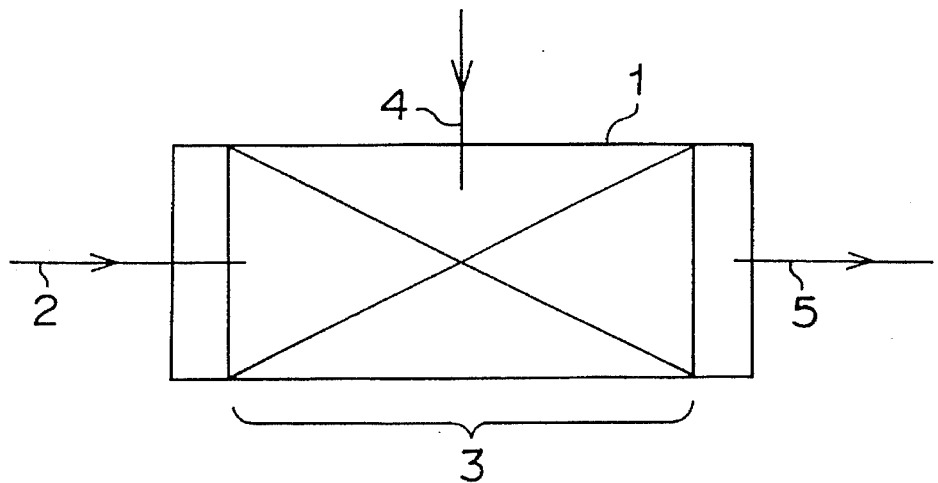
FIG. 1 is a schematic view illustrating a fixed bed flow-through type reactor used in Example 1, Examples 7 to 11, Comparative Example 1, Comparative Examples 5 to 9 and Reference Examples.

Now, the present invention will be described in detail.

The reaction used in the present invention is a gas phase catalytic oxidation reaction of an alkane with ammonia, i.e. an ammoxidation reaction of an alkane. As the alkane, methane, ethane, propane, n-butane, isobutane, pentane, hexane, heptane, or cyclohexane may, for example, be mentioned. Taking the industrial application of the resulting nitrile into consideration, however, it is preferred to employ a $C_{1-4}$ alkane, particularly propane and/or butane, from a viewpoint such that as the resulting nitrile, acrylonitrile and/or methacrylonitrile can be obtained in good yield.

For the ammoxidation reaction of the present invention, it is common to adopt a method wherein an oxygen-containing gas, particularly molecular oxygen, is present in the feed gas. The molecular oxygen to be supplied, may be pure oxygen gas, but it is common to employ air. However, such molecular oxygen may be diluted by an addition of gas inert to the reaction, such as nitrogen, argon or helium.

Further, it is possible to conduct the gas phase catalytic reaction using only an alkane and ammonia as the feed gas, substantially in the absence of the molecular oxygen or in the presence of molecular oxygen in an amount not more than the stoichiometrical amount for converting the alkane to the nitrile. In such a case, it is advisable that a part of the catalyst is appropriately withdrawn from the reaction zone, the catalyst is then supplied to an oxidation regenerator, and after the regeneration, the catalyst is supplied again to the reaction zone. As a method for regenerating the catalyst, a method may, for example, be mentioned wherein an oxidation gas such as oxygen, air or nitrogen oxide is circulated against the catalyst in the regenerator usually at a temperature of from 300° to 600° C.

In a case where propane is mainly used as an alkane and air is used as an oxygen source, the proportion of air to be supplied to the catalyst layer is important for the selectivity for the resulting nitrile. Air is usually at most 25 mol times, preferably from 1 to 20 mol times, against the alkane (i.e. at most about 5 mol times, preferably from 0.2 to 4 mol times, as free oxygen, against the alkane). The total amount of ammonia to be supplied to the reaction is usually from 0.2 to 5 mol times, preferably from 0.5 to 3 mol times, against the alkane. This reaction is carried usually under atmospheric pressure, but can be carried out under elevated pressure or reduced pressure. With respect to other alkanes, other composition of the feed gas may appropriately be selected in accordance with the case of propane.

The method for separately supplying ammonia may vary depending upon the reactor system and is not particularly limited. As the reactor system, a fixed bed system, a fluidized bed system or a mobile bed system may, for example, be employed. Among them, a fixed bed system and a fluidized bed system are common. When these reactor systems are employed, the separate supply of ammonia can be carried out by providing a pipe which supplies the reaction feed gas from the upper stream inlet of the catalyst system and a pipe which supplies a part of the ammonia gas to the interior of the catalyst layer downstream of the reaction feed gas. There is no particular restriction to the shape of the pipe or the supply system for separately supplying ammonia. However, in order to facilitate contact of ammonia with the catalyst or with the reaction feed gas, it is possible to employ a method wherein a number of fine perforations are provided to the supply tube.

In the present invention, downstream from the upper stream inlet of the catalyst layer can not generally be defined due to e.g. the shape of the reactor. Usually, however, in a case where the catalyst layer can be approximated to be of a cylindrical shape, it corresponds to a position located at from ⅓ to ⅘ in the length of the catalyst layer from the upper stream inlet of the catalyst layer. The ammonia to be supplied separately, may be supplied alone or together with the certain amount of an alkane as the reaction gas, oxygen and/or an inert gas such as nitrogen, argon or helium.

In the present invention, it is the most distinguishable feature that using the above mentioned materials for the reaction feed gas, an alkane and ammonia are supplied to an upper stream inlet of the catalyst layer, and at least a part of the total amount of ammonia is separately supplied to a downstream position of the catalyst layer located downstream from the upper stream inlet of the catalyst layer. The amount of the ammonia separately supplied to the downstream position of the catalyst layer located downstream from the upper stream inlet of the catalyst layer, is usually from 5 to 50%, preferably from 10 to 40%, of the total amount of ammonia supplied to the catalyst layer.

By separately supplying ammonia, it is possible to improve the yield of the desired nitrile, particularly the yield of the nitrile per ammonia, which is especially advantageous from the economical viewpoint. The reason for the improvement in yield is not clearly understood. The reason does not seem to be simply such that the opportunity for ammonia to contact the alkane increases as the ammonia is supplied separately. That is, according to the study by the present inventors, even in the method for producing the same nitrile, if the alkane as the starting material is changed to an alkene, such as propylene or isoprene, which has been used commonly heretofore, no improvement is observed in the yield of the nitrile, and the yield rather tends to decrease.

Therefore, it is conceivable that in the production of the nitrile from an alkane, an alkene is produced as an intermediate substance, and conversion of the alkane to the alkene is slower than conversion of the alkene to the nitrile, whereby the supplied ammonia is consumed before it is utilized for the formation of the nitrile by the reaction with alkene. Accordingly, it is conceivable that by supplying a part of ammonia at a downstream position, effective utilization of ammonia can be accomplished.

Further, the reaction for conversion of ammonia to the nitrile is considered to be competing with the reaction for decomposition of ammonia in an oxidizing atmosphere into nitrogen or nitrogen oxide, and if the partial pressure of ammonia is high, the decomposition reaction is more likely to occur. Accordingly, it is conceivable that by dividing the supply of ammonia, a partial pressure of ammonia can be maintained at a low level, whereby decomposition of ammonia can be suppressed, and ammonia can be advantageously utilized for conversion to the nitrile.

Further, in some cases, the nitrile formed under a high partial pressure of ammonia, is likely to be decomposed. Also in such a case, by dividing the ammonia, the partial pressure of the ammonia can be maintained at a low level, whereby decomposition of the nitrile can be suppressed, and consequently, the yield of the nitrile can be improved.

The present invention is commonly applicable to usual ammoxidation reactions of alkanes. Accordingly, conventional catalysts for ammoxidation may generally be useful for the present invention. For example, a number of metal oxide catalysts containing molybdenum and/or vanadium are known. A catalyst containing molybdenum as an essential element may, for example, be a Mo—Bi—P type catalyst (Japanese Unexamined Patent Publication No. 16887/1973), a catalyst obtained by mechanically mixing a V—Sb—W type oxide and a Mo—Bi—Ce—W type oxide (Japanese Unexamined Patent Publication No. 38051/1989), a Mo—Ag—Bi—V type catalyst (Japanese Unexamined Patent Publication No. 58961/1991), a Mo—V—Sn—Bi—P type catalyst (Japanese Unexamined Patent Publication No. 247060/1992), a Mo—Cr—Te type catalyst (U.S. Pat. No. 5,171,876), a composite metal oxide catalyst comprising elements such as Mo and Mn, Co, etc. (Japanese Unexamined Patent Publication No. 194347/1993), a Mo—V—Te—X type catalyst (X is an optional component, Japanese Unexamined Patent Publications No. 257/1990, No. 148212/1993, etc.), a X—Cr—Mo—Bi—Y type catalyst (X is Nb or Ta and Y is an optional component, Japanese Patent Application No. 265192/1992), a Mo—Cr—Bi—X type catalyst (X is an optional component, Japanese Patent Application No. 305361/1993) or Mo—Te—X—Y type catalyst (X is at least one selected from Al, Zr and Ti, and Y is an optional component, Japanese Patent Application No. 309345/1993).

As a catalyst which contains vanadium as an essential component, but does not require molybdenum as an essential component may, for example, be a V—Sb type catalyst (Japanese Unexamined Patent Publication No. 33783/1972, Japanese Examined Patent Publication No. 23016/1975 and Japanese Unexamined Patent Publications No. 28668/1989 and No. 180637/1990), a V—Sb—U—Ni type catalyst (Japanese Examined Patent Publication No. 14371/1972), a V—Sb—W—P type catalyst (Japanese Unexamined Patent Publication No. 95439/1990), a V—Sb—Sn—Cu type catalyst (Japanese Unexamined Patent Publication No. 275266/1992), or a V—W—Te—X type catalyst (X is an optional component, Japanese Patent Publication No. 18918/1993).

Among these, a Mo—V—Te—X type catalyst (a metal oxide catalyst containing molybdenum, vanadium and tellurium) disclosed in, for example, Japanese Unexamined patent Publications No. 257/1990 and No. 103382/1991, is preferred since it is thereby possible to obtain a nitrile, particularly acrylonitrile or methacrylonitrile, at a high selectively even within a relatively low reaction temperature range of from 400° to 450° C. A Mo—V—Te—X type catalyst may be represented by an empirical formula $Mo_{1.0}V_aTe_bX_cO_n$. In the formula, a, b and c represent the atomic ratios of the respective elements per atom of Mo, a is from 0.01 to 1.0, preferably from 0.1 to 0.6, b is from 0.01 to 1.0, preferably from 0.05 to 0.4, c is from 0.0005 to 1.0, preferably from 0.01 to 0.6, and n is a number determined by the oxidized conditions of other elements. Further, component X is at least one element selected from the group consisting of Nb, Ta, W, Ti, Ar, Xr, Cr, Mn, Fe, Ru, Co, Rh, Ni, Pd, Pt, Sb, Bi, B, In and Ce, preferably at least one member selected from the group consisting of Nb, Ta, W, Ti, Sb and Bi.

The above described catalysts show high catalytic performance by themselves, but may be used in combination with a well known carrier, such as silica, alumina, titania, zirconia, aluminosilicate, diatomaceous earth, or boron nitride.

The reaction conditions in the present invention can not generally be defined, since they vary depending upon the above descried reaction gas composition, the type of the catalyst to be used, etc. However, the reaction is carried out usually at a reaction temperature within a range of from 350° to 600° C., preferably from 400° to 500° C. at a gas space velocity SV in the gas phase reaction within a range of from 50 to 10,000 hr$^{-1}$, preferably from 300 to 2,000 hr$^{-1}$.

Now, the present invention will be desired in further detail with reference to Examples. However, it should be understood that the present invention is by no means restricted to such specific Examples.

In the following Examples, the conversion (%), the selectivity (%) and the yield (%) are represented by the following formulas, respectively:

$$\text{Conversion of propane (\%)} = \frac{\text{mols of consumed propane}}{\text{mols of supplied propane}} \times 100$$

$$\text{Selectivity for acrylonitrile (\%)} = \frac{\text{mols of formed acrylonitrile}}{\text{mols of consumed propane}} \times 100$$

$$\text{Yield of acrylonitrile (based on propane) (\%)} = \frac{\text{mols of formed acrylonitrile}}{\text{mols of supplied propane}} \times 100$$

$$\text{Yield of acrylonitrile (based on ammonia) (\%)} = \frac{\text{mols of formed acrylonitrile}}{\text{mols of supplied ammonia}} \times 100$$

EXAMPLE 1

A catalyst having an empirical formula $Mo_1V_{0.3}Te_{0.23}Nb_{0.12}O_n$ (90 wt %)/$SiO_2$ (10 wt %) was prepared as follows.

In 3250 ml of warm water, 789 g of ammonium paramolybdate tetrahydrate, 157 g of ammonium metavanadate and 236 g of telluric acid were dissolved to obtain a uniform aqueous solution. Further, 565 g of silica sol having a silica content of 20 wt % and 1175 g of an aqueous solution of ammonium niobium oxalate having a niobium concentration of 0.456 mol/kg were mixed thereto to obtain a slurry. This slurry was heat-treated to remove water and obtain a solid.

This solid was heat-treated at a temperature of 300° C. until an ammonia odor disappeared and then calcined in a nitrogen stream at 600° C. for 2 hours.

0.55 g of the catalyst thus obtained, was packed into a fixed bed flow-through type reactor as shown in FIG. 1, and a gas phase catalytic reaction was conducted at a reaction temperature of 410° C. by fixing the space velocity SV of the total amount of gas at a level of 680 hr$^{-1}$, and supplying feed gas in a molar ratio of propane:ammonia:air=1:0.7:15 from the pipe 2 of the upper stream inlet of the reactor and further supplying ammonia in an amount of 0.5 mol time of the supplied propane, from the pipe 4 provided at the center of the catalyst layer 3 of the reactor. The gas formed by the reaction, obtained from the pipe 5 of the downstream outlet of the reactor, was analyzed by gas chromatography. The results are shown in Table 1.

COMPARATIVE EXAMPLE 1

0.55 g of the same catalyst as used in Example 1 was packed into the reactor as shown in FIG. 1, and while the reaction temperature and the space velocity of the feed gas were set at the same levels as in Example 1, ammonia was not separately supplied, and a feed gas was supplied in a molar ratio of propane:ammonia:air=1:1.2:15 from the pipe 2 of the upper stream inlet of the reactor. The results are shown in Table 1.

EXAMPLE 2

Figure 2:
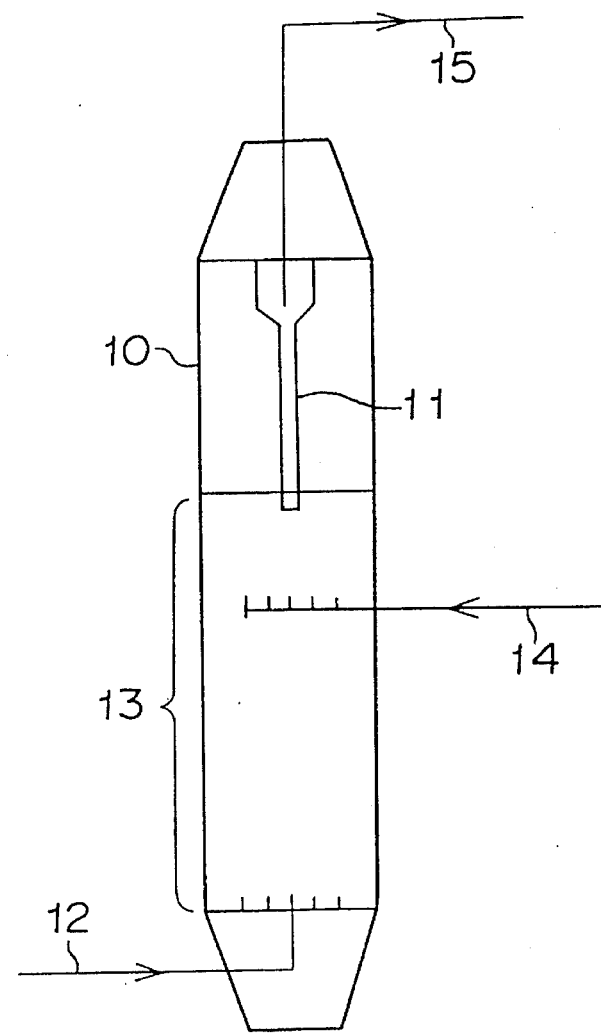
FIG. 2 is a schematic view illustrating a fluidized bed reactor used in Examples 2 to 6 and Comparative Examples 2 to 4.

600 g of the same catalyst as used in Example 1 was packed into a fluidized bed type reactor 10 having a cyclone 11, with the inner diameter of the fluidized catalyst bed section being 52.9 mm, as shown in FIG. 2, and a gas phase catalytic reaction was conducted at a temperature of 445° C. by fixing the weight ratio WWH of supplied propane to the catalyst at a level of about 0.2 g-propane/g-catalyst-hr, and supplying a feed gas in a molar ratio of propane:ammonia:air=1:0.8:15 from a pipe 12 at the bottom of the reactor and further supplying ammonia in an amount of 0.4 mol time of the supplied propane, from the pipe 14 provided at a position located at about ⅔ in height from the bottom of the fluidized catalyst layer 13. The gas formed by the reaction, obtained from the outlet pipe 15 at an upper part of the reactor, was analyzed by gas chromatography. The results are shown in Table 1.

EXAMPLE 3

A gas phase catalytic reaction was conducted in the same manner as in Example 2 except that a feed gas was supplied in a molar ratio of propane:ammonia:air=1:1.0:15 from the pipe 12 at the bottom of the fluidized bed type reactor as shown in FIG. 2, and further ammonia in an amount of 0.2 mol time of the supplied propane was supplied from the pipe 14. The results are shown in Table 1.

COMPARATIVE EXAMPLE 2

A gas phase catalytic reaction was conducted in the same manner as in Example 2 except that ammonia was not separately supplied, and a feed gas was supplied in a molar ratio of propane:ammonia:air=1:1.2:15 from the pipe 12 at the bottom of the fluidized bed type reactor. The results are shown in Table 1.

EXAMPLE 4

A gas phase catalytic reaction was conducted in the same manner as in Example 2 except that a feed gas was supplied in a molar ratio of propane:ammonia:air=1:1.0:15 from the pipe 12 at the bottom of the fluidized bed type reactor, and further ammonia in an amount of 0.1 mol time of the supplied propane, was supplied from the pipe 14. The results are shown in Table 1.

EXAMPLE 5

A gas phase catalytic reaction was conducted in the same manner as in Example 2 except that a feed gas was supplied in a molar ratio of propane:ammonia:air=1:0.8:15 from the pipe 12 at the bottom of the fluidized bed type reactor, and further ammonia in an amount of 0.3 mol time of the supplied propane, was supplied from the pipe 14. The results are shown in Table 1.

COMPARATIVE EXAMPLE 3

A gas phase catalytic reaction was conducted in the same manner as in Example 2 except that ammonia was not separately supplied, and a feed gas was supplied in a molar ratio of propane:ammonia:air=1:1.1:15 from the pipe 12 at the bottom of the fluidized bed type reaction. The results are shown in Table 1.

EXAMPLE 6

A gas phase catalytic reaction was conducted in the same manner as in Example 2 except that a feed gas was supplied in a molar ratio of propane:ammonia:air=1:0.8:15 from the pipe 12 at the bottom of the fluidized bed type reactor, and further ammonia in an amount of 0.2 mol time of the sullied propane, was supplied from the pipe 14. The results are shown in Table 1.

COMPARATIVE EXAMPLE 4

A gas phase catalytic reaction was conducted in the same manner as in Example 2 except that ammonia was not separately supplied, and a feed gas was supplied in a molar ratio of propane:ammonia:air=1:1.0:15 from the pipe 12 at the bottom of the fluidized bed type reactor. The results are shown in Table 1.

TABLE 1

|  | Conversion of propane (%) | Selectivity for acrylo-nitril (%) | Yield of acrylonitrile | |
|---|---|---|---|---|
|  |  |  | Based on propane (%) | Based on ammonia (%) |
| Example 1 | 87.1 | 63.7 | 55.4 | 46.2 |
| Comparative Example 1 | 86.4 | 61.0 | 52.7 | 43.9 |
| Example 2 | 89.0 | 51.5 | 45.8 | 38.2 |
| Example 3 | 88.5 | 51.3 | 45.4 | 37.8 |
| Comparative Example 2 | 88.5 | 50.3 | 44.5 | 37.1 |
| Example 4 | 88.3 | 50.4 | 44.5 | 40.5 |
| Example 5 | 88.2 | 49.7 | 43.8 | 39.8 |
| Comparative Example 3 | 88.0 | 47.7 | 42.0 | 38.2 |
| Example 6 | 88.0 | 49.4 | 43.5 | 43.5 |
| Comparative Example 4 | 88.0 | 47.5 | 41.8 | 41.8 |

EXAMPLE 7

A catalyst having an empirical formula $Mo_1Cr_{0.5}Te_{0.5}Al_8O_n$ was prepared as follows.

In 50 ml of warm water, 2.65 g of ammonium paramolybdate was dissolved to obtain a uniform aqueous solution. To this aqueous solution, 1.72 g of telluric acid, 3.00 g of chromium nitrate nonahydrate and 45.0 g of aluminum nitrate were sequentially added and dissolved. This solution was evaporated to dryness to remove water and obtain a solid. This solid was tabletted and calcined in an air stream at 650° C. for 2 hours.

0.90 g of the catalyst thus obtained, was packed into a fixed bed flow-through type reactor as shown in FIG. 1, and a gas phase catalytic reaction was conducted at a reaction temperature of 500° C. by fixing the space velocity SV of the total amount of gas at a level of 470 hr$^{-1}$, and supplying a feed gas in a molar ratio of propane:ammonia:air=1:0.6:15 from the pipe 2 of the upper stream inlet of the reactor and further supplying ammonia in an amount of 0.6 mol time of the supplied propane, from the pipe 4 provided at the center of the catalyst layer 3 of the reactor. The gas formed by the reaction, obtained from the pipe 5 of the downstream outlet of the reactor, was analyzed by gas chromatography. The results are shown in Table 2.

COMPARATIVE EXAMPLE 5

0.90 g of the same catalyst as used in Example 7 was packed into the reactor as shown in FIG. 1, and while the reaction temperature and the space velocity of the feed gas were set at the same levels as in Example 7, ammonia was not separately supplied, and a feed gas was supplied in a molar ratio of propane:ammonia:air=1:1.2:15 from the pipe 2 of the upper stream inlet of the reactor. The results are shown in Table 2.

EXAMPLE 8

0.90 g of the same catalyst as used in Example 7 was packed into the reactor as shown in FIG. 1, and a gas phase catalytic reaction was conducted in the same manner as in Example 7 except that a feed gas was supplied in a molar ratio of propane:ammonia:air=1:0.6:15 from the pipe 2 of the upper stream inlet of the reactor, and further ammonia in an amount of 0.3 mol time of the supplied propane, was supplied from the pipe 4 provided at the center of the catalyst layer 3 of the reactor. The results are shown in Table 2.

COMPARATIVE EXAMPLE 6

0.90 g of the same catalyst as used in Example 8 was packed into the reactor as shown in FIG. 1, and while the reaction temperature and the space velocity of the feed gas were set at the same levels as in Example 8, ammonia was not separately supplied, and a feed gas was supplied in a molar ratio of propane:ammonia:air=1:0.9:15 from the pipe 2 of the upper stream inlet to the reactor. The results are shown in Table 2.

TABLE 2

|  | Conversion of propane (%) | Selectivity for acrylo-nitril (%) | Yield of acrylonitrile | |
|---|---|---|---|---|
|  |  |  | Based on propane (%) | Based on ammonia (%) |
| Example 7 | 47.2 | 64.3 | 30.4 | 25.3 |
| Comparative Example 5 | 45.7 | 59.7 | 27.3 | 22.8 |
| Example 8 | 46.7 | 61.8 | 28.9 | 32.1 |
| Comparative Example 6 | 45.3 | 45.0 | 20.4 | 22.7 |

EXAMPLE 9

A catalyst having an empirical formula $V_1Sb_5W_1O_n$(50 wt %)—$SiO_2$(10 wt %)—$Al_2O_3$(40 wt %) was prepared as follows.

A small amount of water was mixed to 0.58 g of ammonium metavanadate, 3.64 g of antimony trioxide, 2.32 g of ammonium metatungstate and 5.39 g of silica sol containing 20 wt % of silica, to obtain a slurry. To this slurry, a mixed solution containing 5.07 g of $AlO(OH)_2$ and 0.20 g of acetic acid, was added and mixed. The mixture was evaporated to dryness to remove water and obtain a solid. This solid was tabletted and calcined in an air stream at 550° C. for 3 hours.

0.65 g of the catalyst thus obtained was packed into a fixed bed flow-through type reactor as shown in FIG. 1, and a gas phase catalytic reaction was conducted at a reaction temperature of 480° C. by fixing the space velocity SV of the total amount of gas at a level of 470 hr$^{-1}$, and supplying a feed gas in a molar ratio of propane:ammonia:air=1:0.9:15 from the pipe 2 at the upper stream inlet of the reactor and further supplying ammonia in an amount of 0.3 mol time of the supplied propane, from the pipe 4 provided at the center of the catalyst layer 3 of the reactor. The gas formed by the reaction, obtained from the pipe 5 of the downstream outlet of the reactor, was analyzed by gas chromatography. The results are shown in Table 3.

COMPARATIVE EXAMPLE 7

0.65 g of the same catalyst as used in Example 9 was packed into the reactor as shown in FIG. 1, and while the reaction temperature and the space velocity of the feed gas were set at the same levels as in Example 9, ammonia was not separately supplied, and a feed gas was supplied in a molar ratio of propane:ammonia:air=1:1.2:15 from the pipe 2 of the upper stream inlet of the reactor. The results are shown in Table 3.

TABLE 3

|  | Conversion of propane (%) | Selectivity for acrylonitril (%) | Yield of acrylonitrile | |
|---|---|---|---|---|
|  |  |  | Based on propane (%) | Based on ammonia (%) |
| Example 9 | 75.5 | 38.1 | 28.7 | 23.9 |
| Comparative Example 7 | 78.1 | 34.4 | 26.8 | 22.3 |

EXAMPLE 10

A catalyst having an empirical formula $Nb_{10}Cr_2Mo_{0.48}Bi_{0.40}O_n$(90 wt %)—$SiO_2$(10 wt %) was prepared as follows.

To an aqueous solution having 0.42 g of ammonium paramolybdate dissolved in 41.1 g of silica sol containing 20 wt % of silica, an aqueous solution having 0.97 g of bismuth nitrate pentahydrate dissolved therein, an aqueous ammonium niobium oxalate solution containing 50 mmol of niobium atoms, and an aqueous solution containing 4.02 g of chromium nitrate nonahydrate, were sequentially added and mixed. This mixed solution was evaporated to dryness to remove water and obtain a solid. This solid was tabletted and calcined in an air stream at 600° C. for 2 hours.

0.68 g of the catalyst thus obtained was packed into a fixed bed flow-through type reactor as shown in FIG. 1, and a gas phase catalytic reaction was conducted at a reaction temperature of 480° C. by fixing the space velocity SV of the total amount of gas at a level of 470 hr$^{-1}$, and supplying a feed gas in a molar ratio of propane:ammonia:air=1:0.6:15 from the pipe 2 of the upper stream inlet of the reactor and further supplying ammonia in an amount of 0.6 mol time of the supplied propane, from the pipe 4 provided at the center of the catalyst layer 3 of the reactor. The gas formed by the reaction, obtained from the pipe 5 of the downstream outlet of the reactor, was analyzed by gas chromatography. The results are shown in Table 4.

COMPARATIVE EXAMPLE 8

0.68 g of the same catalyst as used in Example 10 was packed into the reactor as shown in FIG. 1, and while the reaction temperature and the space velocity of the feed gas were set at the same levels as in Example 10, ammonia was not separately supplied, and a feed gas was supplied in a molar ratio of propane:ammonia:air=1:1.2:15 from the pipe 2 of the upper stream inlet of the reactor. The results are shown in Table 4.

EXAMPLE 11

0.68 g of the same catalyst as used in Example 10 was packed into the reactor as shown in FIG. 1, and a gas phase catalytic reaction was conducted in the same manner as in Example 10 except that the feed gas was supplied in a molar ratio of propane:ammonia:air=1:0.6:15 from the pipe 2 of the upper stream inlet of the reactor, and further ammonia in an amount of 0.3 mol time of the supplied propane, was supplied from the pipe 4 provided at the center of the catalyst layer 3 of the reactor. The results are shown in Table 4.

COMPARATIVE EXAMPLE 9

0.90 g of the same catalyst as used in Example 11 was packed into the reactor as shown in FIG. 1, and while the reaction temperature and the space velocity of the feed gas were set at the same levels as in Example 11, ammonia was not separately supplied, and a feed gas was supplied in a molar ratio of propane:ammonia:air=1:0.9:15 from the pipe 2 of the upper stream inlet of the reactor. The results are shown in Table 4.

TABLE 4

|  | Conversion of propane (%) | Selectivity for acrylonitril (%) | Yield of acrylonitrile | |
|---|---|---|---|---|
|  |  |  | Based on propane (%) | Based on ammonia (%) |
| Example 10 | 49.2 | 30.7 | 15.1 | 12.6 |
| Comparative Example 8 | 50.2 | 28.6 | 14.4 | 12.0 |
| Example 11 | 48.0 | 31.9 | 15.3 | 17.0 |
| Comparative Example 9 | 49.7 | 29.2 | 14.5 | 16.1 |

Now, as Reference Examples of the present invention, test examples in which propylene as an alkene was used instead of propane as starting material for the reaction, will be given below.

REFERENCE EXAMPLE 1

A catalyst having an empirical formula $Fe_{10}Cu_{3.5}Sb_{23}Mo_{0.5}W_{0.2}Zn_{0.5}B_{0.5}P_{0.1}Te_{1.3}Si_{55}O_n$ was prepared in accordance with the method disclosed in Japanese Examined Patent Publication No. 49130/1990. 0.50 g of this catalyst was packed into a fixed bed flow-through type reactor as shown in FIG. 1, and a gas phase catalytic reaction was conducted at a reaction temperature of 430° C. by fixing the space velocity SV of the total amount of gas at a level of 500 hr$^{-1}$, and supplying a feed gas in a molar ratio of propylene:ammonia:air=1:0.6:15 from the pipe 2 of the upper stream inlet of the reactor and further supplying ammonia in an amount of 0.6 mol time of the supplied propylene, from the pipe 4 provided at the center of the catalyst layer 3 of the reactor. The gas formed by the reaction, obtained from the pipe 5 of the down stream outlet of the reactor, was analyzed by gas chromatography. The results are shown in Table 5.

REFERENCE EXAMPLE 2

0.50 g of the same catalyst as used in Reference Example 1 was packed into the reactor as shown in FIG. 1, and while the reaction temperature and the space velocity of the feed gas were set at the same levels as in Reference Example 1, ammonia was not separately supplied, and a feed gas was supplied in a molar ratio of propylene:ammonia:air=1:1.2:15 from the pipe 2 of the upper stream inlet of the reactor. The results are shown in Table 5.

REFERENCE EXAMPLE 3

A catalyst having an empirical formula $Mo_{11.86}W_{0.14}Bi_{2.26}Pb_{8.61}Sb_{2.10}Fe_{0.59}O_n/SiO_2$ was prepared in accordance with the method disclosed in Japanese Examined Patent Publication No. 17546/1986. 0.50 g of this catalyst was packed into a fixed bed flow-through type reactor 1 as shown in FIG. 1, and a gas phase catalytic reaction was conducted at a reaction temperature of 460° C. by fixing the space velocity SV of the total amount of gas at a level of 500 $hr^{-1}$, and supplying a feed gas in a molar ratio of propylene:ammonia:air= 1:0.6:15 from the pipe 2 of the upper stream inlet of the reactor and further supplying ammonia in an amount of 0.6 mol time of the supplied propylene, from the pipe 4 provided at the center of the catalyst layer 3 of the reactor. The gas formed by the reaction, obtained from the pipe 5 of the downstream outlet of the reaction, was analyzed by gas chromatography. The results are shown in table 5.

REFERENCE EXAMPLE 4

0.50 g of the same catalyst as used in Reference Example 3 was packed into the reactor as shown in FIG. 1, and while the reaction temperature and the space velocity of the feed gas were set at the same levels as reference example 3, ammonia was not separately supplied, and a feed gas was supplied in a molar ratio of propylene:ammonia:air=1:1.2:15 from the pipe 2 of the upper stream inlet of the reactor. The results are shown in Table 5.

REFERENCE EXAMPLE 5

0.50 g of a catalyst having an empirical formula $Mo_1Cr_{0.5}Te_{0.5}Al_8O_n$ shown in Example 7, was packed in a fixed bed flow-through type reactor as shown in FIG. 1, and a gas phase catalytic reaction was conducted at a reaction temperature of 480° C. by fixing the space velocity SV of the total amount of gas at a level of 500 $hr^{-1}$, and supplying a feed gas in a molar ratio of propylene:ammonia:air=1:0.6:15 from the pipe 2 of the upper stream inlet of the reactor and further supplying ammonia in an amount of 0.6 mol time of the supplied propylene, from the pipe 4 provided at the center of the catalyst layer of the reactor. The gas formed by the reaction, obtained from the pipe 5 of the downstream outlet of the reactor, was analyzed by gas chromatography. The results are shown in Table 5.

REFERENCE EXAMPLE 6

0.50 g of the same catalyst as used in Reference Example 5 was packed into the reactor as shown in FIG. 1, and while the reaction temperature and the space velocity of the feed gas were set at the same levels as in Reference Example 5, ammonia was not separately supplied, and a feed gas was supplied in a molar ratio of propylene:ammonia:air=1:1.2:15 from the pipe 2 of the upper stream inlet of the reactor. The results are shown in Table 5.

From comparison of the foregoing Reference Examples specifically comparison with Reference Examples 1 and 2, Reference Examples 3 and 4 and Reference Examples 5 and 6, it is apparent that when an alkene was used as starting material, no improvement in the yield of the nitrile was observed by the separate supply of ammonia to the reactor, and the yield thereby rather decreased.

TABLE 5

|  | Conversion of propylene (%) | Selectivity for acrylonitril (%) | Yield of acrylonitrile | |
|---|---|---|---|---|
|  |  |  | Based on propylene (%) | Based on ammonia (%) |
| Reference Example 1 | 96.2 | 86.6 | 83.3 | 69.4 |
| Reference Example 2 | 95.4 | 88.2 | 84.1 | 70.1 |
| Reference Example 3 | 97.5 | 76.4 | 74.5 | 62.1 |
| Reference Example 4 | 97.8 | 85.5 | 83.6 | 55.7 |
| Reference Example 5 | 98.2 | 34.1 | 33.5 | 27.9 |
| Reference Example 6 | 98.3 | 50.6 | 49.7 | 41.4 |

By adopting the method of the present invention, it is possible to improve the yield of a nitrile by a gas phase catalytic reaction of an alkane with ammonia. Particularly, it is thereby possible to effectively convert ammonia to the nitrile.

What is claimed is:

1. A method for producing an α, β-ethylenically unsaturated nitrile by a gas phase catalytic oxidation reaction of an alkane with ammonia in the presence of an ammoxidation catalyst, which comprises:

supplying an alkane of at least three carbon atoms, in the presence of elemental oxygen and ammonia to a reactor having an alkane, oxygen, ammonia mixed gas inlet and an ammonia inlet, each inlet being upstream of the ammoxidation catalyst bed in the reactor with the ammonia inlet positioned between the mixed gas inlet and the position of the catalyst layer, said ammonia, which is supplied to the reactor through the ammonia inlet, ranging in an amount of 5 to 10 mol % of the total amount of ammonia supplied to the reactor.

2. The method for producing a nitrile according to claim 1, wherein the total amount of ammonia supplied to the catalyst layer is from about 0.2 to about 5 mol times against the alkane.

3. The method for producing a nitrile according to claim 1, wherein an oxygen-containing gas is supplied to the mixed gas inlet of the catalyst layer.

4. The method for producing a nitrile according to claim 3, wherein the amount of the oxygen-containing gas supplied to the mixed gas inlet of the catalyst layer is from 0.2 to 4 mol times as free oxygen against the alkane.

5. The method for producing a nitrile according to claim 1, wherein the catalyst is a metal oxide catalyst containing molybdenum and/or vanadium.

6. The method for producing a nitrile according to claim 1, wherein the catalyst is a metal oxide catalyst containing molybdenum, vanadium and tellurium.

7. The method for producing a nitrile according to claim 1, wherein the catalyst is a metal oxide catalyst containing vanadium and antimony.

8. The method for producing a nitrile according to claim 1, wherein the alkane is propane and/or butane.

9. The method for producing a nitrile according to claim 1, wherein at least a part of the total amount of ammonia is supplied to a position of the catalyst layer located at from $1/5$ to $4/5$ of the length of the catalyst layer from the mixed gas inlet of the catalyst layer.

* * * * *